United States Patent [19]
George

[11] Patent Number: 4,742,819
[45] Date of Patent: May 10, 1988

[54] INTUBATING SCOPE WITH CAMERA AND SCREEN

[76] Inventor: Gordon P. George, 1717 North 1030 West, Orem, Utah 84057

[21] Appl. No.: 29,205

[22] Filed: Mar. 23, 1987

[51] Int. Cl.$^4$ ............................................. A61B 1/04
[52] U.S. Cl. ......................................... 128/6; 128/11; 358/98
[58] Field of Search .......................... 128/4, 6, 10, 11; 358/98

[56] References Cited

U.S. PATENT DOCUMENTS

| | | | |
|---|---|---|---|
| 3,776,222 | 12/1973 | Smiddy | 128/6 |
| 4,086,919 | 5/1978 | Bullard | 128/11 |
| 4,567,882 | 2/1986 | Heller | 128/11 |
| 4,573,452 | 3/1986 | Greenberg | 128/6 X |

*Primary Examiner*—William H. Grieb
*Attorney, Agent, or Firm*—K. S. Cornaby

[57] ABSTRACT

A fiber optic intubating scope with camera and screen is used in the intubation of an endotracheal tube in patients whose larynges are not easily viewed with a laryngoscope because of morphological irregularities or complications. Use of the invention in intubation of such patients in emergency situations facilitates exact placement of the endotrachael tube by providing a screen-displayed image of the patient's pharynx and larynx, and further allows the physician to simultaneously monitor the internal placement of the endotracheal tube and the external conditions of the patient. The intubation process, facilitated by use of the invention, can be accomplished via the pharynx of nasopharynx. In alternative embodiments, the invention can be powered from a peripheral source or can be powered by means of a self-contained power source pack. The invention has both emergency and non-emergency intubation application, as well as utility in the form of a bronchoscope.

8 Claims, 3 Drawing Sheets

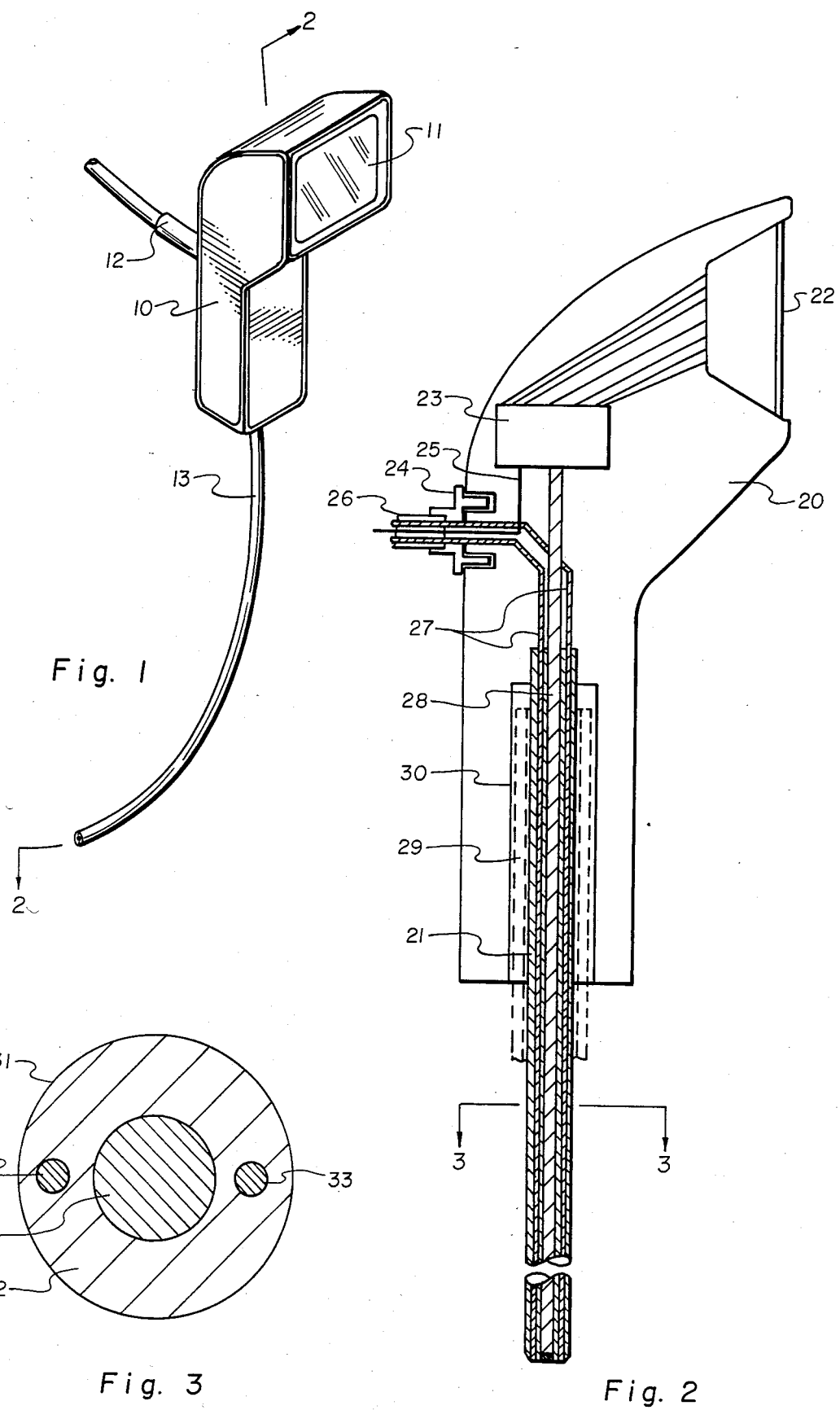

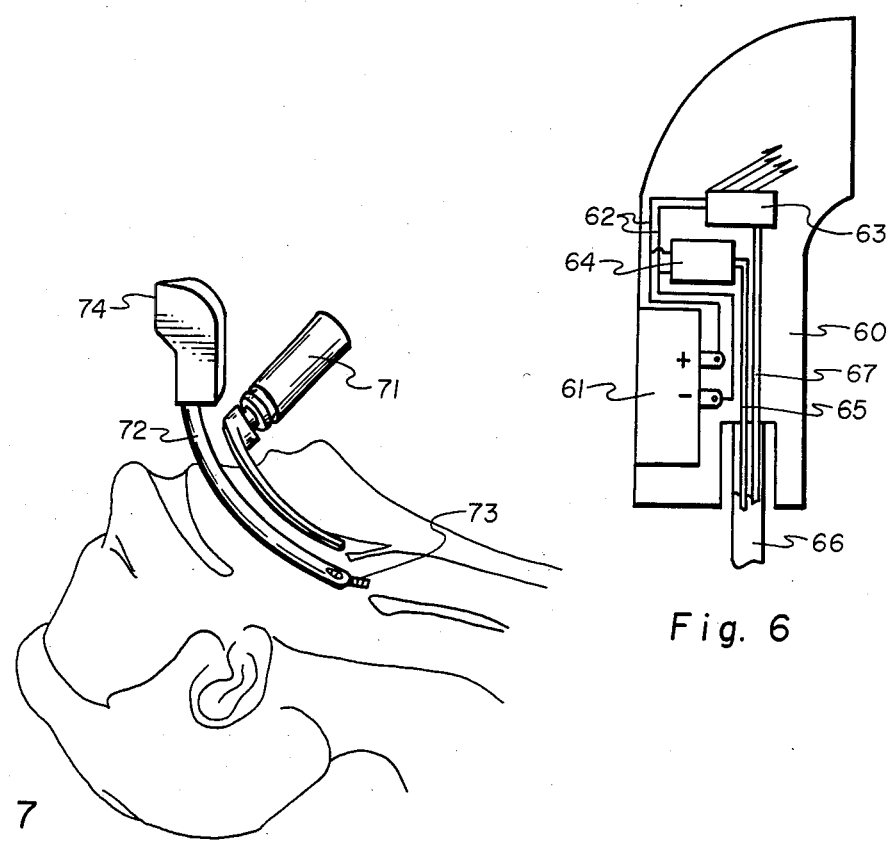
Fig. 7
Fig. 6
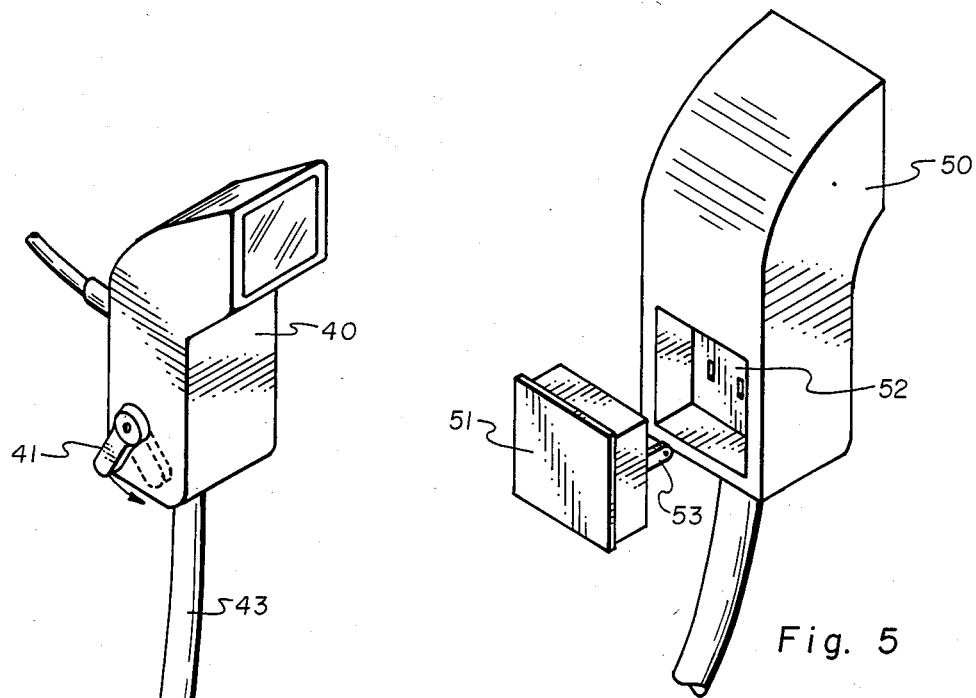
Fig. 4
Fig. 5

INTUBATING SCOPE WITH CAMERA AND SCREEN

BACKGROUND OF THE INVENTION

This invention relates to fiber optic scopes and intubation in medical, as well as potentially non-medical, applications.

It is frequently necessary in standard medical procedures to insert an endotracheal tube into the trachea of a patient for the purpose of performing diagnostic tests or for the introduction of some means of ventilation assistance. Even in the best of situations, such intubation is often difficult and can give rise to complications in the patient. Aspiration of stomach contents into the trachea and an inability to expeditiously intubate the patient, leading to significant hypoxemia, are examples of attendant complications. There have also been cases of death related to complications arising from intubation.

In many patients, intubation is particularly formidable due to morphological anomalies, such as a large tongue, excessive soft tissue, or tracheal displacement which makes it difficult to visualize the posterior pharyngeal area and larynx. In emergency medical situations, attempts to intubate such persons is difficult, time consuming, and often meets with failure. It is the purpose of the invention herein to provide a means of intubation, facilitated by an optical system, in those types of patients whose pharynx, larynx, and trachea are not easily visualized.

Devices for facilitating patient intubation through visual means have been disclosed in prior art, most notably U.S. Pat. No. 3,776,222 to Smiddy, entitled "Fiber Optic Entubator and Method of Entubation of the Trachea Through the Nasopharynx". That invention involves the introduction of an endotracheal tube through the nasopharynx, facilitated by an internally disposed fiber optic scope with a single eyepiece viewing means at the proximal end. The invention therein disclosed was devised for use in situations where the patient could assist in placement of the endotracheal tube by swallowing action when the patient is in an upright position. In emergency situations, assistance from the patient, even one able to maintain an upright posture, is unlikely. Intubation must be quick, and accomplished by mechanical means guided only by the attending physician or technician. Further, the invention disclosed in U.S. Pat. No. 3,776,222 makes use of a single eyepiece for viewing that which is illuminated by the fiber optic system, much like the single eyepiece of a telescope. If the attending physician removes his eye from the eyepiece to make an external assessment of the patient, a critical lapse in time occurs before the physician can refocus the internal image produced in the eyepiece. Such a lapse of time can affect the timely placement of the endotracheal tube and may even cause the physician to miss or misinterpret certain landmarks such that exact placement of the tube is hindered.

In the present invention, a camera disposed within the optical housing projects the image illuminated by the fiber optic system onto a television-like screen. This arrangement negates the need for focusing and refocusing the eye upon the objective, and allows a simultaneous viewing of the internal and external condition of the patient during the intubation procedure. In many applications, this invention has preferable use over existing fiber optic scopes, such as the bronchoscope and laryngoscope, because of the immediacy with which it can be put into operation. Existing bronchoscopes require a preparatory setup which is time consuming, and expertise in their use limits their effectiveness.

Modifications of the fiber optic system in this invention allows intubation through either the pharynx or nasopharynx in both emergency situations and intubations where the patient is awake. Further, modifications of the fiber optic system of the invention allow its use as bronchoscope, in non-emergency applications, for exploration, diagnostic testing, and surgical procedure.

It is an objective of this device to provide a means of visually facilitating the intubation of an endotracheal tube via the pharynx or nasopharynx in emergency situations in those types of patients whose larynx is difficult to view through use of a laryngoscope alone due to morphological irregularities or complications.

It is further an objective of this invention to provide a means of viewing through the camera the opening to the tracheal airway of the patient while being simultaneously capable of viewing the airway of the patient through use of a television-type screen illuminating the internal image.

It is further an objective to provide a margin of safety to the physician in successful placement of an endotracheal tube in an emergency situation in those types of patients whose larynx is difficult to view through use of a laryngoscope alone.

It is further an object of this device to provide a means of optically facilitating emergency intubations without the delay in setup of the instrument which is inherent in existing fiber optic scopes.

It is a further objective of this device to provide a means of optically facilitating endotracheal intubation in emergency situations by use of a unit with a self-contained power source.

Yet another objective is to provide a means of optically facilitating endotracheal intubation via the pharynx or nasopharynx in non-emergency situations in those types of patients who larynx is difficult to view through use of a laryngoscope alone due to morphological irregularities or complications.

Another objective of this invention is to provide a fiber optic bronchoscope device for use in non-emergency situations which allows the physician to simultaneously view the patient's internal tract while viewing the external condition of the patient by means of a television-type viewing screen.

SUMMARY OF THE INVENTION

The intubation scope herein disclosed is composed of a camera/screen housing unit from which emerges a semi-malleable or flexible tube containing the fiber optic bundles of the fiber optic system. It is over this fiber optic tube that a standard hollow endotracheal tube is slideably disposed. When the endotracheal tube is fitted on the fiber optic tube, one end of the endotracheal tube fits into a space within the bottom portion of the camera/screen housing unit. In this embodiment, the fiber optic tube extends just beyond the distal end of the endotracheal tube so that the tube serves as a "stylet" for inserting the endotracheal tube.

The light source to the fiber optic bundles and the power source to the camera are provided by means of a peripheral power source plugged into the camera/screen housing unit. Alternatively, the apparatus may be powered by a self-contained power source and light source which plugs into the camera/screen housing unit.

The initial placement of the endotracheal tube into the pharynx is facilitated by the use of a laryngoscope. After the laryngoscope has been inserted, the distal end of the endotracheal tube, slideably disposed onto the fiber optic tube is guided into the pharynx and guided further into the larynx by viewing the image illuminated on the screen.

Light projected through the descending fiber optic bundles passes through their length to the tip of the fiber optic tube. Light from the illuminated tract travels back through the fiber optic tube to the camera where the image is focused and projected onto the screen. Varying flexibility and length of the fiber optic tube allows the device to be used as a bronchoscope in non-emergency situations, for diagnostic and therapeutic purposes. These and other uses of the invention will become more obvious through consideration of the drawings of preferred embodiments.

THE DRAWINGS

Preferred embodiments of the invention are illustrated in the attached drawings, in which:

FIG. 1 is a perspective view of the invention;

FIG. 2 is a cross-sectional view of the invention taken at Line 2—2 of FIG. 1;

FIG. 3 is a transverse cross-sectional view of the fiber optic tube taken at Line 3—3 of FIG. 2;

FIG. 4 is a perspective view of the invention in an alternative embodiment showing a lever for manipulation of the distal end of the fiber optic tube;

FIG. 5 is a partially exploded perspective view of an alternative embodiment in which the apparatus is operated by its own power source.

FIG. 6 is a lateral cross-sectional view of the camera/screen housing unit illustrating the internal electrical and light source configuration in the alternative embodiment illustrated in FIG. 5;

FIG. 7 is an illustration of the intubation procedure via the pharynx; and

DETAILED DESCRIPTION OF THE PREFERRED EMBODIMENTS

Figure 8:
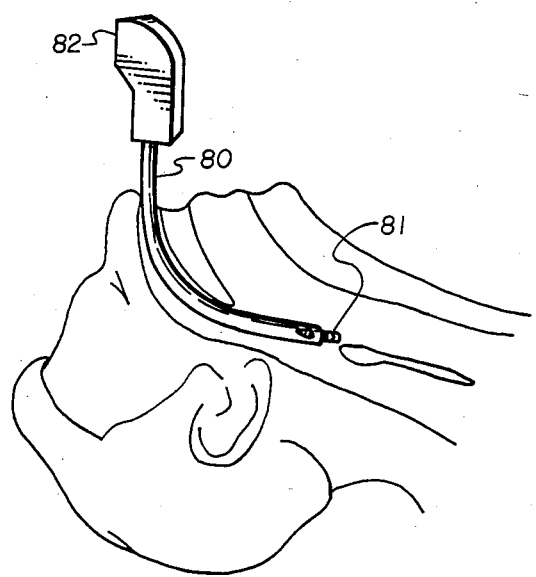
FIG. 8 is an illustration of the intubation procedure via the hasopharynx.

FIG. 1 is an illustration of the invention showing the camera/screen housing unit 10. The viewing screen II is located at the upper end of the housing, opposite to the efferent peripheral power source 12 which enters into the back of the camera/screen housing unit. The peripheral power source will be more fully illustrated in FIG. 2. The fiber optic tube 13 is shown emerging from the housing unit.

FIG. 2 is a cross-sectional illustration of the camera/screen housing unit 20 and emerging fiber optic tube 21. The front, upper face of the housing unit is fitted with a screen 22 onto which is projected the image focused in the camera 23. The fiber optic system of the scope is powered, in this embodiment, by a peripheral power source 24 which is shown plugged into the back of the housing unit. The peripheral power source contains an electrical line 25 which powers the camera, and a light source 26 which illuminates the fiber optic bundles 27. Light travels down the fiber optic bundles embedded in the fiber optic tube, illuminates the surrounding area, and the light from the illuminated area travels upwardly through the centrally located fiber optic channel 28, into the camera where the image is focused and projected onto the screen. The endotracheal tube 29, shown in plantom, is slideably disposed upon the fiber optic tube and fits into a recess 30 formed in the lower portion of the housing unit around the fiber optic tube.

FIG. 3 is a transverse cross-sectional view through the fiber optic tube 31. Embedded within the tube, surrounded by a semi-malleable material 32, are the light transmitting fiber optic bundles 33, and the centrally located fiber optic bundle 34 which carries light reflected by the illuminated environment to the camera.

FIG. 4 is an illustration of an alternative embodiment showing the camera/screen housing unit 40 fitted with a lever 41 on the side of the housing which operates to cause movement at the distal end of the fiber optic tube 42. In this illustration, the endotracheal tube 43 is shown encircling the fiber optic tube.

FIG. 5 is a view of the camera/screen housing unit 50 from the side opposite the screen. In this embodiment, a self-contained power source pack 51 is illustrated, and is shown to plug into the housing unit at an interfacingly recessed facet 52. Electrical contact between the power source and the internal circuitry of the scope is accomplished through a set of prongs 53. The descending tube 54 is also illustrated.

FIG. 6 is a cross-sectional illustration of the housing unit 60 showing the self-contained power source pack 61 in place within the housing unit. Electrical circuits 62 integrate with the power source and feed both the camera 63 and integral light source 64. The illuminated light transmitting fiber optic bundles 65 emerge from the light source and descend through the fiber optic tube 66. The fiber optic bundle 67 which returns the light to the camera for imaging is shown.

FIG. 7 illustrates insertion of the fiber optic scope through the patient's pharynx with aid of a laryngoscope 71. The endotracheal tube 72 is fitted over the fiber optic tube, the distal end of which forms the "stylet" 73. The image thus produced is visible on the screen 74 at the front of the housing unit.

FIG. 8 illustrates insertion of the fiber optic scope through the patient's nasopharynx, where the endotracheal tube 80 is fitted upon the fiber optic tube, the distal end of which forms the "stylet" 81. Again, the image produced may be viewed on the screen 82 at the front of the housing unit.

I claim:

1. An intubating scope comprising in combination:
a housing adapted to be hand-held;
screen means contained in said housing;
camera means contained in said housing for transmitting light images to said screen;
semi-malleable hollow tube means connected at one end thereof to said housing;
at least one fiber optic tube disposed within said malleable tube means, said fiber optic tube connected at one end thereof to said camera means for providing light images from the opposite end of said fiber optic tube to said camera means; and
a power source connected to said camera and fiber optic tube.

2. A scope as set forth in claim 1, wherein a bundle of fiber optic tubes are contained in said semi-malleable tube and are attached to said camera means.

3. A scope as set forth in claim 1, wherein said semi-malleable hollow tube is an endoctracheal tube for intubating an individual's throat.

4. A scope as set forth in claim 1, wherein said power source is contained in said housing.

5. A scope as set forth in claim 1, wherein said power source is disposed outside said housing and is connected to said camera and fiber optic tube.

6. A scope as set forth in claim 1, wherein the end of the fiber optic tube opposite the end connected to said camera extends beyond the end of the semi-malleable tube and can be manipulated by lever means connected to said housing.

7. A scope as set forth in claim 1, wherein said camera means comprises a cathode ray tube type camera.

8. A scope as set forth in claim 1, wherein said camera means comprises an electron scanning type camera.

* * * * *